United States Patent [19]

Frank et al.

[11] 4,058,128
[45] Nov. 15, 1977

[54] ELECTRODE

[76] Inventors: Howard A. Frank, 319 Longwood Ave., Boston, Mass. 02115; Paul M. Zoll, 1101 Beacon St., Brookline, Mass. 02146

[21] Appl. No.: 718,142

[22] Filed: Aug. 26, 1976

[51] Int. Cl.² ............................................. A61N 1/04
[52] U.S. Cl. ............................... 128/418; 128/419 P
[58] Field of Search ............... 128/418, 419 P, 404, 128/2.06 E, 2.1 E, DIG. 4

[56] References Cited

U.S. PATENT DOCUMENTS

| | | | |
|---|---|---|---|
| 3,216,424 | 11/1965 | Chardack | 128/418 |
| 3,253,595 | 5/1966 | Murphy, Jr. et al. | 128/418 X |
| 3,580,242 | 5/1971 | La Croix | 128/2.06 F |
| 3,737,579 | 6/1973 | Bolduc | 128/418 |
| 3,844,292 | 10/1974 | Bolduc | 128/418 |
| 3,978,865 | 9/1976 | Trabucco | 128/419 P |

OTHER PUBLICATIONS

Introduction to Bioelectrodes, Plenum Press, N.Y., 1974, pp. 182–184.

Primary Examiner—Robert W. Michell
Assistant Examiner—Lee S. Cohen

[57] ABSTRACT

An electrode useful inter alia for secure and reliable implantation in a human heart which has a barb element sharp in one longitudinal direction and dull in the other, and a placement element alongside the barb and spaced a predetermined distance from it.

5 Claims, 7 Drawing Figures

ELECTRODE

BACKGROUND OF THE INVENTION

This invention relates to electrodes, and most particularly to electrodes that may usefully be lodged in, for example, the human heart, for cooperation with a pacemaker. There has long been need for such a device characterized by improved ease of implantment and reliability of performance.

Two prior art electrode patents that are of interest are Bolduc U.S. Pat. No. 3,844,292.

SUMMARY OF THE INVENTION

The invention features an electrode having a longitudinally extending barb shaft with a barb sharp at one end and not at the other and a placement element extending alongside said barb shaft. In preferred embodiments the placement element is of silicone rubber, has a flat surface parallel with the barb shaft, and has small holes extending through it.

The invention has numerous advantages. It permits lodging the electrode in the thin atrium wall. Alternatively, still through an easily tolerated single small access portal in the pericardium, it can be lodged in a thin right ventricular wall. Lodging is positive and reliable. Axial rotation is prevented. Good electrical contact exists. The electrode moves complexly with the heart, millions of times per year, resisting both dislodgment and formation of impaired tissue (as results from relative movement). Positioning is extremely precise, with the barb along a path generally parallel to the heart wall. Use of very flexible leads is permitted.

PREFERRED EMBODIMENT

We turn now to drawings and description of a preferred embodiment of the invention.

DRAWINGS

DESCRIPTION

Figure 1:
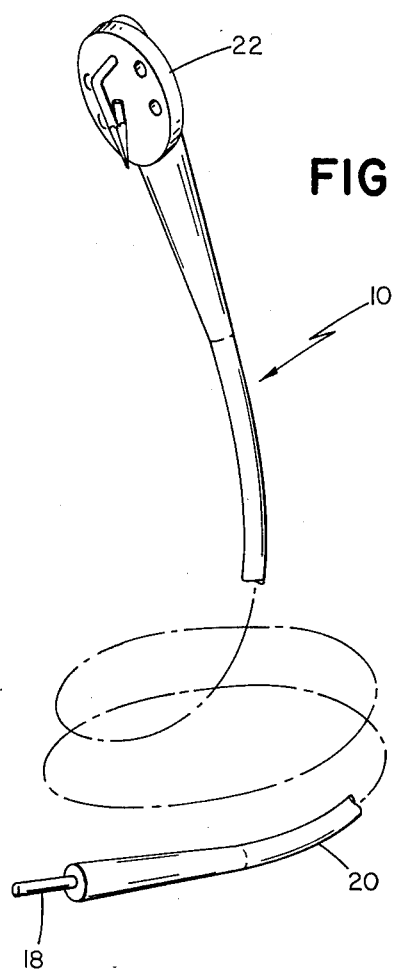
FIG. 1 is a perspective view, partially broken away, of a preferred embodiment of electrode according to the invention.

The presently preferred embodiment of the electrode is indicated generally at 10.

A barb element, indicated generally at 12, is secured, through sleeve 14 (at 14a), inside the wrappings of lead 16, which in turn is secured in crimped connections to the sleeve at 14b and (not shown) to connector tip 18. Lead 16 is surrounded by silicone rubber covering 20, which is enlarged and shaped toward the barb end of the electrode to provide a placement element 22.

Lead 16 is formed of flat ribbons of platinum: iridium alloy, wound around a central non-conductive core, of the general character described in Bolduc U.S. Pat. No. 3,572,344, "Electrode Apparatus with Novel Lead Construction", granted Mar. 23, 1971. Barb element 12 and sleeve 14 are formed from the same alloy as lead 16.

The barb element 12 includes barb shaft 24, mounting shaft 26, and spacing shaft 28; the latter shaft extends generally perpendicularly to the two other shafts. Barb 30 is carried by barb shaft 24, and terminates in sharpened point 32 facing longitudinally of the electrode toward its connector tip end and flat surface 34 facing in a generally opposite direction.

Thin sleeves of silicone rubber (not shown) are provided (applied while xylene-soft) over the straight portions of shaft 28, to reduce the threshold current.

Figure 5:
FIG. 5 is a cross-sectional view of a set of crimping tools for use in making said embodiment.
Figure 6:
FIG. 6 is a cross-sectional view of another set of crimping tools for use in making said embodiment.

In assembling the lead to the barb element, the nonconductive center of lead 16 was removed far enough longitudinally to make room for the end of mounting shaft 26 of the barb element. It was then inserted into the end of the lead, and sleeve 14 secured thereover at crimped portion 14a with the crimping tool shown in FIG. 6; the crimp 14b of sleeve to lead was by the crimping tool shown in FIG. 5. In making the barb element, the point was initially formed by heating together two rods, one bent at 20°, until a ball was formed at the tip; the point was then formed, and the flat surface 34.

In the embodiment shown, spacing shaft 28 was about 7/32 inches in length; its distance from surface 44 was about 5/32 inches.

Figure 2:
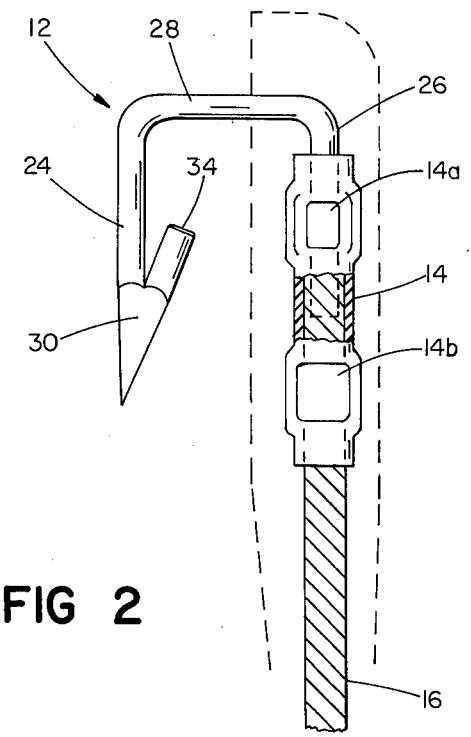
FIG. 2 is a view, partly in side elevation, partly broken away (within the dashed line, and toward its connector end), and partly in section, of said embodiment.
Figure 4:
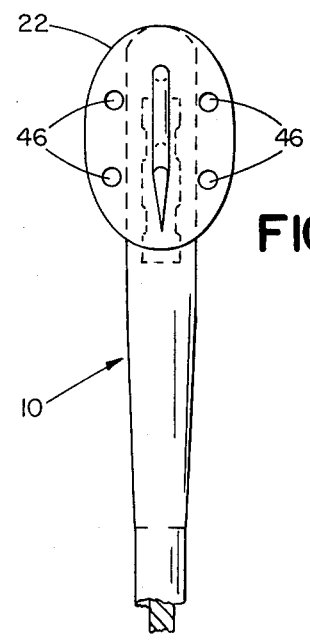
FIG. 4 is a front elevation view, partially broken away, thereof.
Figure 7:
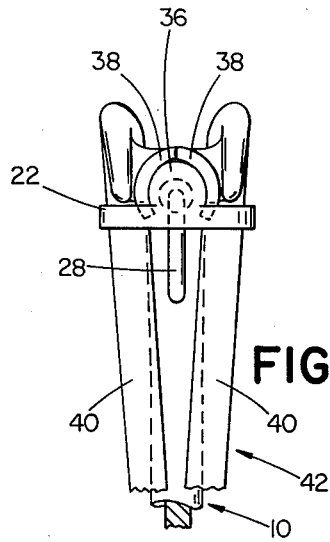
FIG. 7 is an end view, partially broken away, of the barb end of said embodiment being held in a holding clamp, for implantation in a heart wall.
Figure 3:
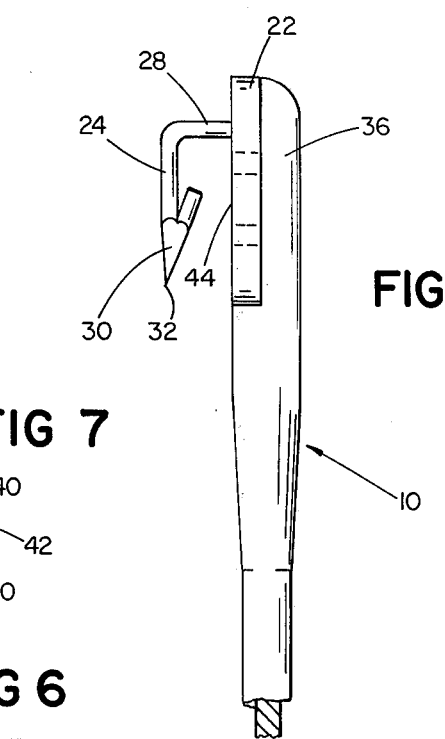
FIG. 3 is a side elevation view, partially broken away, thereof.

In operation, a surgeon makes a small, easily tolerated incision, exposing the pericardium. The barb end of an electrode is held, at its rounded portion 36 adjacent its placement element 22, in the two rounded jaw portions 38 carried by the two legs 40 of the scissors-like (with clamping ratchet adjacent thumb and finger holes) holding clamp indicated generally at 42. Barb 30 may then be inserted into an atrial of ventricular wall in an angular way, until placement surface 44 of placement element 22 engages the heart wall; the device may then be pushed to "ski" along on surface 44 until spacing shaft 28 stops movement. The portion of the barb element outside the dotted lines of FIG. 2 is then firmly implanted in the heart wall, without perforation, with precise positioning. Not only blunt portion 34 but surface 44 as well helps hold the barb in its inserted position from the start; surface 44 prevents axial rotation; and within a short time, further, tissue grows around the electrode and into holes 46 to further assist in anchoring the electrode.

OTHER EMBODIMENTS

Other embodiments within the invention will occur to those skilled in the art. For example, the barb may be formed entirely of suitable plastic, secured onto a metal barb shaft by any suitable means; it may even be that this will be the most preferred means.

CLAIMS

What is claimed is:

1. An electrode comprising a barb element adapted to be inserted into an organ of a mammal, a placement element to slidingly engage said organ during insertion of said barb element, and transversely extending connecting means for connecting a first extremity of said barb element and said placement element and lead means electrically connected to said connecting means for connection to an electrical instrument, said barb element including a longitudinally extending shaft and a barb at a second extremity of said barb element, said barb being sharp in a longitudinal direction away from said first extremity for easy insertion into the body of the mammal and blunt in the opposed longitudinal direction to hold said barb in its inserted position, said placement element providing a substantially fixed placement-defining surface extending longitudinally alongside said barb shaft and being transversely spaced therefrom by said connecting means a predetermined amount to gauge and limit the extent of depth of insertment of said barb and the direction of insertion of said shaft into the body and to hold said barb in position and against rotation in said organ, and said barb element and said connecting means being electrically conductive.

2. The electrode of claim 1 in which said placement-defining surface is of silicone rubber.

3. The electrode of claim 1 in which said placement element includes at least one tissue hole extending therethrough.

4. The electrode of claim 1 in which said barb is flat in said opposed longitudinal direction.

5. The electrode of claim 1 in which said placement element includes at least one tissue hole extending therethrough, said placement-defining surface is of silicone rubber, and said barb is flat in said opposed longitudinal direction.

* * * * *